United States Patent
Sloman et al.

(10) Patent No.: US 8,170,671 B2
(45) Date of Patent: May 1, 2012

(54) METHOD AND SYSTEM FOR OVERDRIVING A HEART CHAMBER DURING A THRESHOLD SEARCH ACCORDING TO AN AV DELAY

(75) Inventors: Laurence S. Sloman, West Hollywood, CA (US); Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 512 days.

(21) Appl. No.: 12/483,976

(22) Filed: Jun. 12, 2009

(65) Prior Publication Data

US 2010/0318152 A1    Dec. 16, 2010

(51) Int. Cl.
*A61N 1/08*    (2006.01)
(52) U.S. Cl. .................................................. 607/28
(58) Field of Classification Search ............... 607/27–28
See application file for complete search history.

(56) References Cited

U.S. PATENT DOCUMENTS

| | | | |
|---|---|---|---|
| 5,766,229 A | 6/1998 | Bornzin | |
| 6,615,089 B1 | 9/2003 | Russie et al. | |
| 6,928,326 B1 | 8/2005 | Levine | |
| 6,950,704 B1 | 9/2005 | Bradley | |
| 6,963,775 B2 | 11/2005 | Russie et al. | |
| 6,973,350 B1 | 12/2005 | Levine et al. | |
| 7,006,869 B2 | 2/2006 | Bradley | |
| 7,035,687 B1 | 4/2006 | Levine et al. | |
| 7,286,876 B2 | 10/2007 | Yonce et al. | |
| 7,412,287 B2 | 8/2008 | Yonce et al. | |
| 2004/0148109 A1 | 7/2004 | Fischer | |
| 2006/0149328 A1 | 7/2006 | Parikh et al. | |
| 2006/0224193 A1 | 10/2006 | Hess | |
| 2010/0100148 A1* | 4/2010 | Min et al. ........................ 607/27 |

FOREIGN PATENT DOCUMENTS

| WO | 2006069032 A1 | 6/2006 |
|---|---|---|
| WO | 2007073514 A1 | 6/2007 |

OTHER PUBLICATIONS

Kam, Ruth, "Automatic Capture Verification in Pacemakers (Autocapture)—Utility and Problems," Indian Pacing Electrophysioly J. Apr.-Jun. 2004:;4(2):73-78.

* cited by examiner

*Primary Examiner* — Carl H Layno
*Assistant Examiner* — Jessica Sarcione (57) ABSTRACT

An implantable medical device includes a lead, a pulse generator, an autothreshold module and a control module. The lead includes electrodes positioned within a heart. At least one of the electrodes senses cardiac signals. The pulse generator delivers a stimulus pulse through at least one of the electrodes. The autothreshold module performs a threshold search when operating in an autothreshold mode and causes atrial stimulus pulses to be delivered in an atrium of the heart at an overdrive rate during the threshold search. The control module determines an AV conduction time and applies an overdrive AV adjustment to the AV conduction time to generate an AV delay. The autothreshold module uses the AV delay in connection with delivering ventricular stimulus pulses to a ventricle of the heart.

22 Claims, 8 Drawing Sheets

METHOD AND SYSTEM FOR OVERDRIVING A HEART CHAMBER DURING A THRESHOLD SEARCH ACCORDING TO AN AV DELAY

CROSS-REFERENCE TO RELATED APPLICATIONS

This application is related to co-pending U.S. patent application Ser. No. 12/483,995, filed concurrently herewith, titled "Method and System for Automatically Switching Between Modes of an Implantable Medical Device".

FIELD OF THE INVENTION

Embodiments of the present invention generally pertain to implantable medical devices and more particularly to methods and systems that apply stimulus pulses to chambers of a heart.

BACKGROUND OF THE INVENTION

An implantable medical device (IMD) is implanted in a patient to monitor, among other things, electrical activity of a heart and to deliver appropriate electrical therapy, as required. Implantable medical devices include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. These pulses are referred to as stimulus or stimulation pulses.

The stimulus pulses are delivered to chambers of the heart at a stimulus output. The stimulus output represents the strength or electrical potential of the stimulus pulses. If the stimulus output of the pulses is not sufficiently large, then the stimulus pulses may be ineffective. Stimulus pulses having an output that does not exceed a stimulation threshold of the heart may not cause polarization of one or more chambers of the heart or propagate. For example, a stimulus pulse applied to a ventricle at a stimulus output that is less than the stimulation threshold of the heart may not result in depolarization of the ventricle, or capture in the ventricle.

In order to ensure that stimulus pulses are delivered to the heart at electric potentials that exceed the stimulation threshold of the heart, the IMD may periodically adjust the stimulus output of the pulses. The IMD may invoke an autothreshold mode. In the autothreshold mode, the IMD performs a threshold search that adjusts the electric potential of stimulus pulses applied to the heart after the threshold search is completed. The threshold search adjusts the stimulus output of the pulses such that the pulses have an output that is at least as great as the stimulation threshold.

A threshold search in some known IMDs incrementally decreases the electric potential of pulses in consecutive cardiac cycles until a predetermined number of consecutive losses of capture are detected. For example, the stimulus output at which stimulus pulses are applied to a ventricle of the heart may be decreased by 0.25 or 0.3 Volts for each cardiac cycle until a loss of capture is detected. If a loss of capture is detected in a cardiac cycle, some known IMDs deliver a back-up stimulus pulse to the ventricle to ensure ventricular contraction during the cardiac cycle. Once the loss of capture is detected, the same stimulus output may be used for the next cardiac cycle to determine if another loss of capture occurs. If the loss of capture continues to occur for the predetermined number of consecutive cardiac cycles, then the losses of capture may indicate that the current stimulus output is below the stimulation threshold. In some known IMDs, the predetermined number of consecutive cardiac cycles is two. On the other hand, if the loss of capture does not occur in the following cardiac cycle, the stimulus output continues to be decreased in subsequent cardiac cycles until loss of capture occurs in the predetermined number of consecutive cardiac cycles.

Once the stimulus output is decreased such that loss of capture occurs for the predetermined number of cardiac cycles, the stimulus output is then incrementally increased. The stimulus output is increased for each cardiac cycle until capture is detected. For example, the stimulus output may be increased by 0.125 or 0.3 Volts for each cardiac cycle until capture is detected. Additional stimulus pulses are applied at the current stimulus output until capture occurs in a predetermined number of cardiac cycles. In some known IMDs, the predetermined number of cardiac cycles is two. The stimulation threshold is then set to be equal to this stimulus output. Additional stimulus pulses are applied at stimulus outputs that are at least as great as this newly established stimulation threshold. In some known IMDs, the additional stimulus pulses are supplied to the heart at levels that are at least 0.25 or 0.3 Volts above the stimulation threshold.

During the threshold search, stimulation pulses that do not result in capture in the ventricle within a predetermined time period after applying the stimulus pulse are followed with delivery of a back-up stimulus pulse. The back-up stimulus pulse is applied to the ventricle to ensure that the ventricle does contract or polarize. If the stimulus pulse is supplied at a sufficiently large stimulus output, the stimulus pulse will result in ventricular capture. But, delivery of the stimulus pulse and an intrinsic ventricular contraction may occur at approximately the same time and become conflated, or fused with one another.

The fusion of intrinsic and paced ventricular contractions may hamper the ability of the IMD to accurately perform the threshold search. Fusion may cause a captured ventricular contraction to appear as a non-captured ventricular contraction caused by a ventricular stimulus pulse. Alternatively, a non-captured ventricular contraction caused by a ventricular stimulus pulse may appear as a captured ventricular contraction.

Some known IMDs shorten the AV interval and/or PV interval during pacing associated with a threshold search in an effort to avoid fusion. The reduction of the AV and/or PV intervals is referred to as AV/PV shortening. AV/PV shortening may cause patient discomfort during threshold searches due to the relatively short AV and PV intervals. Shortening the AV and PV intervals frequently does not result in good hemodynamic response of the heart and may cause patients to be symptomatic.

A need exists for an improved threshold search that avoids fusion while maintains adequate hemodynamic response of the heart to improve patient comfort during the threshold search.

BRIEF SUMMARY OF THE INVENTION

In one embodiment, an implantable medical device is provided. The device includes a lead, a pulse generator, an autothreshold module and a control module. The lead includes electrodes positioned within a heart. At least one of the electrodes senses cardiac signals. The pulse generator delivers a stimulus pulse through at least one of the electrodes. The autothreshold module performs a threshold search when operating in an autothreshold mode and causes atrial stimulus pulses to be delivered in an atrium of the heart at an overdrive rate during the threshold search. The control module determines an AV conduction time and applies an overdrive AV adjustment to the AV conduction time to generate an AV delay. The autothreshold module uses the AV delay in connection with delivering ventricular stimulus pulses to a ventricle of the heart.

In another embodiment, a method for overdriving a heart chamber during a threshold search is provided. The method includes delivering stimulus pulses to an atrium of the heart at an overdrive rate during the threshold search and determining an AV conduction time based on the stimulation pulses. The method also includes applying an overdrive AV adjustment to the AV conduction time to generate an AV delay and utilizing the AV delay in connection with delivering a stimulus pulse to a ventricle of the heart.

In another embodiment, a computer readable storage medium for use with an implantable medical device having a lead including electrodes configured to be positioned within a heart, a pulse generator and a microcontroller is provided. The computer readable storage medium includes instructions to direct the pulse generator to deliver atrial stimulus pulses in an atrium of the heart at an overdrive rate during a threshold search. The instructions also direct the microcontroller to determine an AV conduction time and apply an overdrive AV adjustment to the AV conduction time to generate an AV delay. The instructions direct the pulse generator to utilize the AV delay in connection with delivering ventricular stimulus pulses to a ventricle of the heart.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided for overdriving a heart chamber during a threshold search. In one embodiment, systems and methods described herein overdrive an atrium of the heart to reduce fusion of paced and intrinsic ventricular contractions during ventricular threshold searches.

Figure 1:
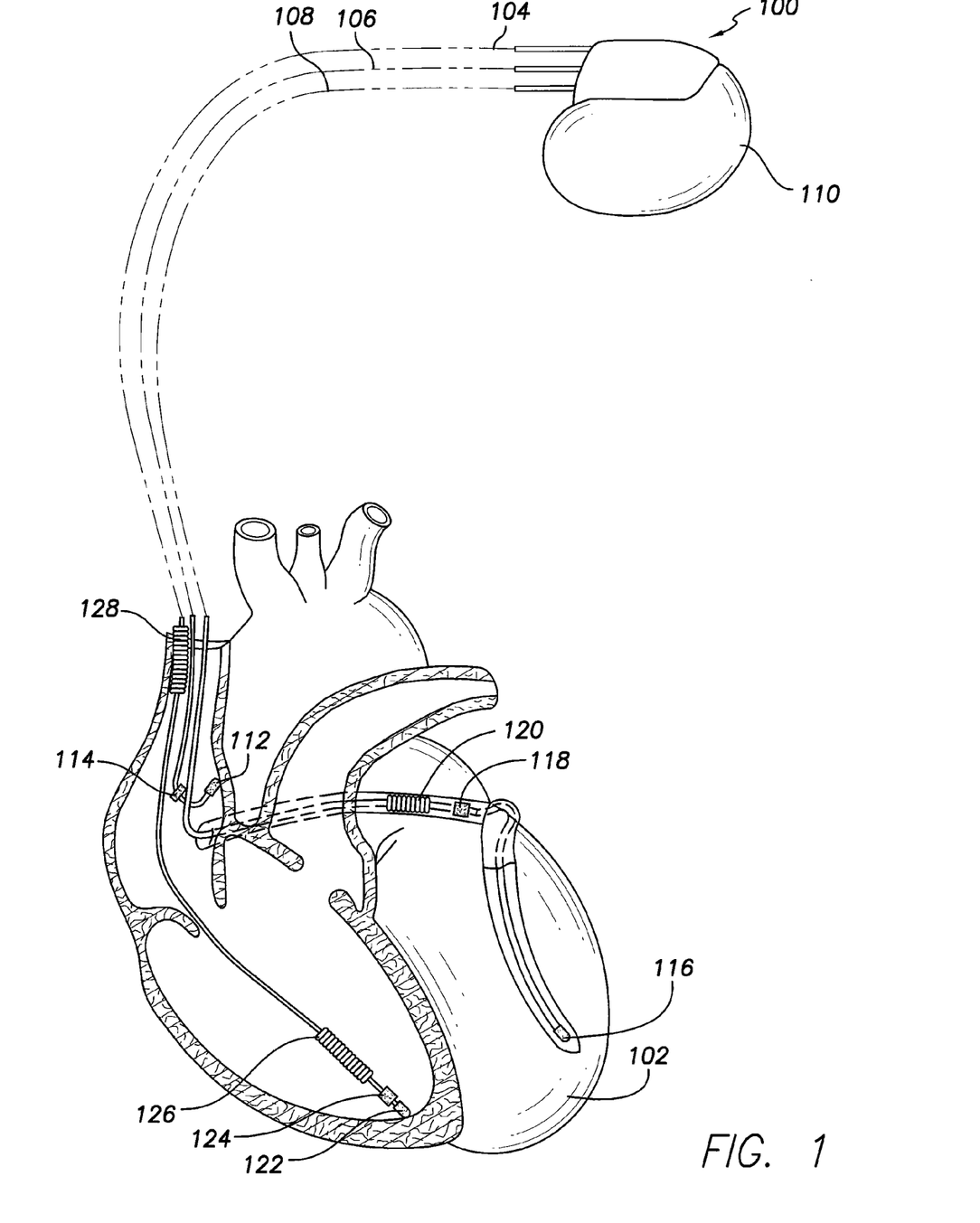
FIG. 1 illustrates an implantable medical device (IMD) coupled to a heart in accordance with one embodiment.

FIG. 1 illustrates an implantable medical device (IMD) 100 coupled to a heart 102 in accordance with one embodiment. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like. The IMD 100 includes a housing 110 that is joined to several leads 104, 106, 108. The leads 104, 106, 108 are located at various locations of the heart 102, such as an atrium, a ventricle, or both, to measure cardiac signals of the heart 102. The leads 104, 106, 108 include the right ventricular (RV) lead 104, the right atrial (RA) lead 106, and the coronary sinus lead 108. Several electrodes are coupled with the leads 104, 106, 108 for sensing cardiac signals and/or for delivering stimulus or stimulation pulses to the heart 102. The housing 110 may be one of the electrodes and is often referred to as the "can", "case", or "case electrode."

The RV lead 104 is coupled with an RV tip electrode 122, an RV ring electrode 124, and an RV coil electrode 126. The RV lead 104 may include a superior vena cava (SVC) coil electrode 128. The right atrial lead 106 includes an atrial tip electrode 112 and an atrial ring electrode 114. The coronary sinus lead 108 includes a left ventricular (LV) tip electrode 116, a left atrial (LA) ring electrode 118 and an LA coil electrode 120. Alternatively, the coronary sinus lead 108 may be a quadropole lead that includes several electrodes disposed within the left ventricle. Leads and electrodes other than those shown in FIG. 1 may be included in the IMD 100 and positioned in or proximate to the heart 102.

The IMD 100 monitors cardiac signals of the heart 102 to determine if and when to deliver stimulus pulses to one or more chambers of the heart 102. The IMD 100 may deliver pacing stimulus pulses to pace the heart 102 and maintain a desired heart rate and/or shocking stimulus pulses to treat an abnormal heart rate such as tachycardia or bradycardia. The stimulus pulses are supplied to the heart 102 at a stimulus output. The stimulus output is the magnitude of the stimulus pulses. For example, a stimulus output may be approximately 1.0 Volt. The stimulus output needs to be periodically checked and/or updated to ensure that the stimulus output exceeds a stimulation threshold. The stimulation threshold represents the minimum stimulus output required to capture the stimulus pulse in one or more chambers of the heart. The stimulation threshold may be an intrinsic characteristic of the heart 102 that changes over time. If a pacing stimulus pulse is delivered to a ventricle at a stimulus output that is at least as great as the stimulation threshold, then the pulse may be captured in the ventricle to cause ventricular depolarization. On the other hand, if the pulse is delivered at a stimulus output that is less than the stimulation threshold, then the pulse may not result in ventricular capture.

In order to ensure that stimulus pulses are delivered to the heart 102 at stimulus outputs that are at least as great as the stimulation threshold, the IMD 100 may switch to an autothreshold mode. In the autothreshold mode, the IMD 100 performs a threshold search that adjusts the stimulus output of the stimulus pulses over multiple cardiac cycles. The threshold search adjusts the stimulus output of the pulses such that the pulses have an output that is at least as great as the stimulation threshold. In one embodiment, a threshold search includes incrementally decreasing the stimulus output of stimulus pulses in consecutive cardiac cycles until a predetermined number of consecutive losses of capture are detected. For example, the stimulus output at which stimulus pulses are applied to a chamber of the heart 102 may be decreased by 0.25 or 0.3 Volts for each cardiac cycle until a loss of capture in the same chamber is detected. If a loss of capture is detected, the IMD 100 may deliver a back-up stimulus pulse to the chamber. Once the loss of capture is detected, the same stimulus output is used for the next cardiac cycle to determine if another loss of capture occurs. If the loss of capture continues to occur for the predetermined number of consecutive cardiac cycles, then the losses of capture may indicate that the current stimulus output is below the stimulation threshold. In one embodiment, the predetermined number of consecutive cardiac cycles is two. Alternatively, if the loss of capture does not occur in the following cardiac cycle, the stimulus output continues to be decreased in subsequent cardiac cycles until loss of capture occurs in the predetermined number of consecutive cardiac cycles.

Once the stimulus output is decreased such that loss of capture occurs for the predetermined number of cardiac cycles, the stimulus output is then incrementally increased. The stimulus output is increased for each cardiac cycle until capture is detected. For example, the stimulus output may be increased by 0.125 or 0.3 Volts for each cardiac cycle until capture is detected. Additional stimulus pulses are applied at the current stimulus output until capture occurs in a predetermined number of cardiac cycles. In one embodiment, the predetermined number of cardiac cycles is two. The stimulation threshold is then set to be equal to this stimulus output. Additional stimulus pulses are applied at stimulus outputs that are at least as great as this newly established stimulation threshold. Alternatively, the stimulus pulses are delivered at a predetermined level above the stimulation threshold. For example, additional stimulus pulses may be supplied to the heart 102 at levels at least 0.25 or 0.3 Volts above the stimulation threshold.

Fusion may occur during threshold searches and conflate the capture of a stimulus pulse in a ventricle with application of a back-up stimulus pulse applied to the ventricle. For example, the back-up stimulus pulse that is applied to a ventricle may occur at or during the same time period or window during which the ventricle intrinsically contracts or polarizes. Fusion may cause the IMD 100 to miss a captured stimulus pulse during the threshold search. In order to reduce fusion during a threshold search and reduce the number of captured stimulus pulses that are missed by the IMD 100, the IMD 100 may overdrive an atrium of the heart 102. For example and as described below, the IMD 100 may increase the rate at which stimulus pulses are applied to an atrium to increase the conduction time at which the stimulus pulses propagate from the atrium to the corresponding ventricle. The increased conduction time provides additional time for the stimulus pulse to be captured in a ventricle before a back-up stimulus pulse is applied to the ventricle.

Figure 2:
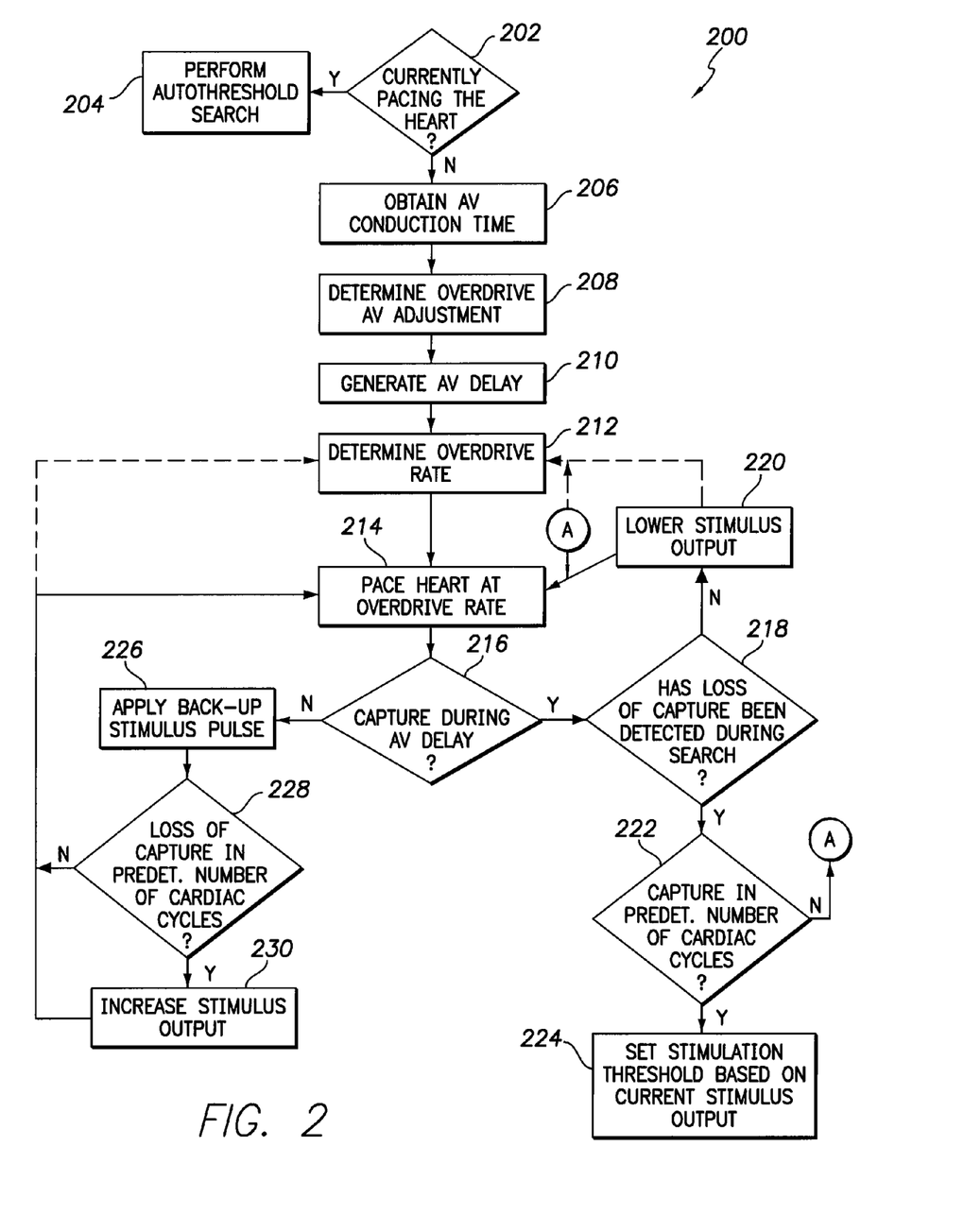
FIG. 2 is a flowchart of a process for performing a threshold search in accordance with one embodiment.

FIG. 2 is a flowchart of a method 200 for performing a threshold search in accordance with one embodiment. The method 200 may be initiated to commence the threshold search when a loss of capture is detected in at least two consecutive cardiac cycles. Alternatively, the threshold search is initiated periodically. For example, the threshold search may be performed every eight hours if no loss of capture is detected in two or more consecutive cardiac cycles during the preceding eight hour time period. In another embodiment, the threshold search is manually initiated by an operator of the IMD 100. A physician may manually commence the threshold search using an external device such as an external device 540 shown in FIG. 5 and described below.

At 202, a determination is made as to whether the IMD 100 (shown in FIG. 1) is currently pacing an atrium of the heart 102 (shown in FIG. 1). If the IMD 100 is currently pacing an atrium at regular intervals, such as once during each cardiac cycle, then additional pacing or more frequent pacing of the atrium during a threshold search may be unnecessary. For example, overdriving the atrium while conducting a threshold search may be unnecessary. As a result, in one embodiment, at 204, the threshold search is performed as described above without overdriving the atrium. On the other hand, if the IMD 100 is not actively pacing an atrium at regular or periodic intervals, then the threshold search is performed with overdriving an atrium. For example, if the IMD 100 is monitoring the frequency or rate at which P-waves occur in the cardiac signals of the heart 102 rather than actively pacing an atrium, then the method 200 may overdrive an atrium during the threshold search.

At 206, an AV conduction time is obtained. The AV conduction time is the time period between delivery of an atrial stimulus pulse and a corresponding ventricular event. For example, the AV conduction time may be the time period extending from application of the atrial stimulus pulse to capture of the pulse in a corresponding ventricle.

Figure 3:
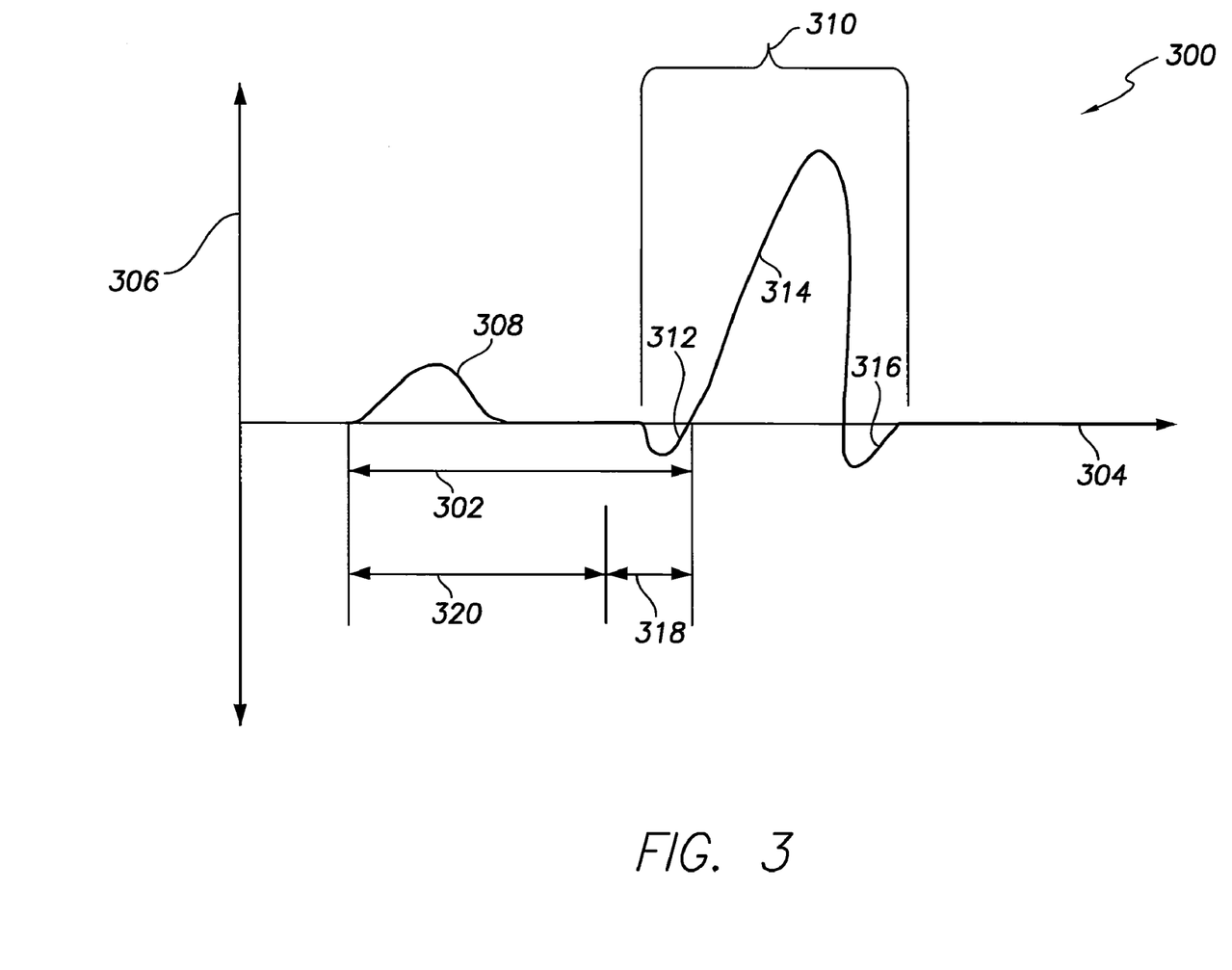
FIG. 3 illustrates an example of a cardiac signal that is monitored by the IMD shown in FIG. 1.

FIG. 3 illustrates an example of a cardiac signal 300 that is monitored by the IMD 100 (shown in FIG. 1) to obtain an AV conduction time 302 of the heart 102. The cardiac signal 300 is shown alongside a horizontal axis 304 representative of time and a vertical axis 306 representative of the strength or magnitude of the cardiac signal 300. The cardiac signal 300 includes a P-wave 308 that is representative of atrial activity of the heart 102. The QRS complex 310 represents ventricular contraction of the heart 102 that follows the P-wave 308.

Returning to the discussion of the method 200 shown in FIG. 2 with continued reference to the cardiac signal 300 of FIG. 3, at 206, the AV conduction time 302 may be obtained by determining the time period between the P-wave 308 and the R-wave 314 of the QRS complex 310. For example, the IMD 100 (shown in FIG. 1) may monitor the cardiac signal 300 to identify when the P-wave 308 begins and when the R-wave 314 begins and calculate the AV conduction time 302 based thereon. The IMD 100 may determine when the P-wave 308 and R-wave 314 begin based on the morphology of the waveforms of the cardiac signal 300. For example, the IMD 100 may identify the beginning of the waveforms of the P-wave 308 and the R-wave 314 by comparing each waveform to one or more waveform templates that are representative of a P-wave or an R-wave. Based on the similarities and/or differences between the waveforms of the cardiac signal 300 and the waveform templates, the IMD 100 may identify the P-wave 308 and the R-wave 314.

In the event that the atrial stimulus pulse applied at 206 does not result in a corresponding ventricular depolarization, the method 200 may continue to apply atrial stimulus pulses at increasing stimulus outputs until capture results. For example, the IMD 100 (shown in FIG. 1) may incrementally increase the electrical potential of stimulus pulses until ventricular depolarization occurs and the AV conduction time 302 can be measured. Alternatively, the IMD 100 may deliver the atrial stimulus pulse at 206 at a predetermined magnitude or level above the current stimulus output of the stimulus pulses. For example, if, prior to 206, the IMD 100 was supplying stimulus pulses to the heart 102 at 0.5 Volts, the IMD 100 may deliver the atrial stimulus pulse at 206 at 0.8 or 1.0 Volts (or some other predetermined value above the current stimulus output). The IMD 100 may apply the atrial stimulus pulse at the larger stimulus output to ensure capture in the ventricle so that the AV conduction time 302 can be measured.

At 208, an overdrive AV adjustment 318 is determined. The overdrive AV adjustment 318 represents a modification to the AV conduction time 302. The overdrive AV adjustment 318 is used to determine when to apply a back-up ventricular stimulus pulse in the event of a loss of capture in a ventricle. For example and as described below, the overdrive AV adjustment 318 may be used to determine how long to wait for capture of an atrial stimulus pulse in the ventricle before the IMD 100 (shown in FIG. 1) determines that a loss of capture has occurred. The overdrive AV adjustment 318 may be a predetermined time period stored in a memory accessible by the IMD 100. Alternatively, the overdrive AV adjustment 318 may be a function of the AV conduction time 302. For example, the overdrive AV adjustment 318 may increase and decrease in a linear or non-linear relationship with the AV conduction time 302. The overdrive AV adjustment 318 may be dynamically modified during the threshold search based on a previously measured AV conduction time 302. For example, if the AV conduction time 302 changes during a threshold search, the overdrive AV adjustment 318 may similarly be adjusted.

At 210, an AV delay 320 is generated. As described below, the AV delay 320 is used by the IMD 100 (shown in FIG. 1) during overdriving of the heart 102 (shown in FIG. 1) to determine whether to apply a back-up stimulus pulse to a ventricle. For example, the AV delay 320 may represent the time period or window that begins at the commencement of an atrial event such as the P-wave 308. During overdriving of an atrium, the IMD 100 monitors the cardiac signals 300 of the heart 102 over the AV delay 320 to determine if capture of the atrial stimulus pulse occurs. If no ventricular capture is detected by the IMD 100 during the AV delay 320, then the IMD 100 may apply a back-up stimulus pulse to the ventricle.

The AV delay 320 may be generated by shortening the AV conduction time 302 by the overdrive AV adjustment 318. Alternatively, the AV delay 320 is generated by modifying the AV conduction time 302 by a linear or non-linear function of the overdrive AV adjustment 318. The AV delay 322 in one cardiac cycle may be based on the AV conduction time 302 measured during a prior cardiac cycle.

At 212, an overdrive rate of the heart 102 (shown in FIG. 1) is determined. The overdrive rate is the rate or frequency at which stimulus pulses are applied to the heart 102 to overdrive the heart 102. For example, the IMD 100 (shown in FIG. 1) may deliver stimulus pulses to an atrium of the heart 102 at the overdrive rate to overdrive the heart 102. The overdrive rate may be a predetermined value. For example, the overdrive rate may be a predetermined heart rate stored in a memory accessible by the IMD 100.

Alternatively, the overdrive rate is based on a cardiac rate of the heart 102. For example, the overdrive rate may be based on the rate or frequency at which an atrium contracts or polarizes. The IMD 100 obtains the cardiac rate by measuring the rate or frequency in which P-waves occur in the cardiac signals monitored by the IMD 100. The cardiac rate is measured over a predetermined number of cardiac cycles. For example, the cardiac rate can be the average cardiac rate that is measured over ten consecutive cardiac cycles. In one embodiment, the cardiac rate may be dynamically updated during the threshold search. An overdrive margin is applied to the cardiac rate to generate the overdrive rate. For example, the measured cardiac rate may be increased by the overdrive margin to obtain the overdrive rate. The overdrive margin may be a predetermined amount stored in a memory of the IMD 100. By way of example only, the overdrive margin may be at least 5 beats per minute. Alternatively, the overdrive margin may be based on the cardiac rate. For example, the overdrive margin may be a multiple of a standard deviation of the cardiac rate measured over a predetermined number of cardiac cycles. The overdrive margin is dynamically updated during the threshold search. If the cardiac rate increases or decreases during the threshold search, the overdrive margin may be updated in response thereto.

A threshold search is performed in connection with the operations at 216-230 of the method 200. As described below, the threshold search is conducted by overdriving the heart 102 (shown in FIG. 1) to increase the AV conduction time 302 of the heart 102. When a chamber of the heart 102, such as an atrium, is paced at the overdrive rate, the stimulus pulses are delivered to the heart chamber at the overdrive rate. If the stimulus pulses are applied to an atrium, the stimulus pulses cause polarization of the atrium. The stimulus output of the atrial stimulus pulses may propagate through the myocardium from the atrium to a corresponding ventricle. If the atrial stimulus pulses are applied at a sufficiently high stimulus output (for example, at an electrical potential that exceeds the stimulation threshold of the heart 102), arrival of the stimulus pulse in the ventricle results in capture. Capture of the stimulus output causes ventricular contraction or polarization. As shown in FIG. 3, the AV conduction time 302 may represent the time period required by a stimulus pulse applied to an atrium to propagate through the heart 102, arrive in a ventricle, and cause ventricular contraction.

Pacing an atrium of the heart 102 (shown in FIG. 1) at a rate that exceeds the intrinsic heart rate, or rate of contraction of the heart 102, can increase the AV conduction time 302 (shown in FIG. 3). For example, the time required for an atrial stimulus pulse to travel from an atrium to a corresponding ventricle may be increased when the atrium is paced with stimulus pulses at a rate that exceeds the intrinsic rate of contraction of the atrium. On the other hand, the AV conduction time for intrinsic cardiac events may be less than the AV conduction time 302 for paced cardiac events. For example, in contrast to pacing an atrium of the heart 102, the intrinsic contraction of the atrium may result in the propagation of electrical signals through the heart 102 to a corresponding ventricle in less time than would otherwise be achieved if the atrium were paced by the IMD 100 (shown in FIG. 1).

During a threshold search, overdriving a chamber of the heart 102 (shown in FIG. 1), such as an atrium, may increase the time required for the paced atrial stimulus pulses to propagate through the heart 102 to a corresponding ventricle. For example, pacing an atrium at the overdrive rate may increase the AV conduction time 302 (shown in FIG. 3) of the heart 102. Increasing the AV conduction time 302 may provide a greater time period or window over which an intrinsic ventricular response can occur. For example, while an atrium of the heart 102 is paced at the overdrive rate, the AV conduction time 302 may be increased, which in turn increases the AV delay 320. As the AV delay 320 increases, the IMD 100 (shown in FIG. 1) is provided with an increased time period or window over which to monitor cardiac signals of the heart 102 for capture of an atrial stimulus pulse in a ventricle before the IMD 100 applies a back-up stimulus pulse to the ventricle. Increasing the time period or window over which the IMD 100 monitors the cardiac signals before applying the back-up stimulus pulses may reduce the occurrence of fusion between paced ventricular events caused by the back-up stimulus pulses and intrinsic ventricular events caused by capture of atrial stimulus pulses in the ventricle.

Figure 4:
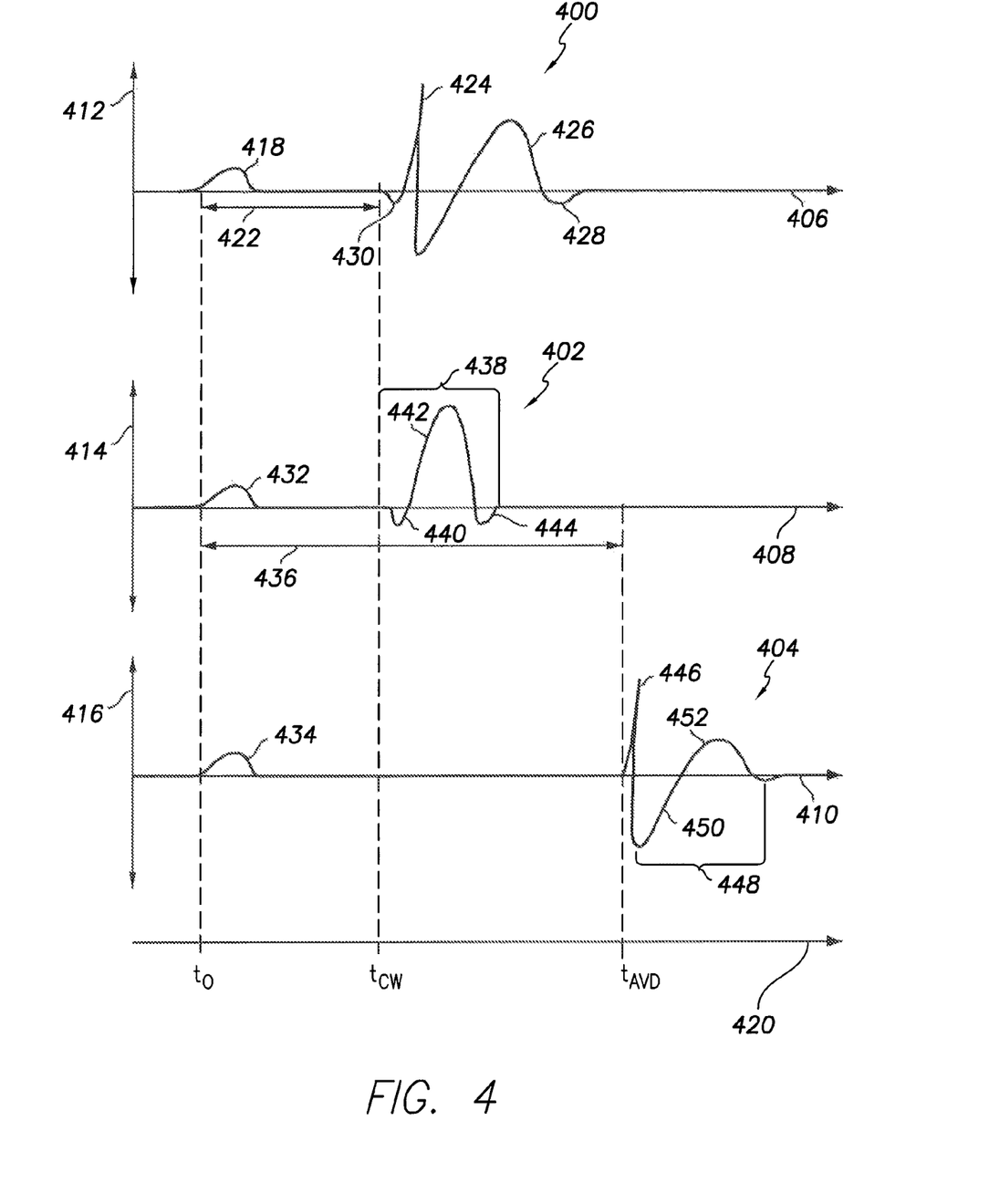
FIG. 4 is an example of three cardiac signals each sensed over a single cardiac cycle in accordance with one embodiment.

FIG. 4 is an example of three cardiac signals 400-404 each sensed over a single cardiac cycle in accordance with one embodiment. The cardiac signals 400-404 are described below to demonstrate the occurrence of fusion between paced and intrinsic ventricular events and the impact of overdriving the heart 102 (shown in FIG. 1) during a threshold search. For example, the first cardiac signal 400 is described below to demonstrate the occurrence of fusion between paced and intrinsic ventricular events. The second and third cardiac signals 402, 404 are described below to demonstrate an increase in AV conduction time 302 (shown in FIG. 3) and AV delay 320 (shown in FIG. 3) brought about by overdriving the heart 102. Each of the cardiac signals 400-404 is illustrated alongside a corresponding horizontal axis 406-410 and a vertical axis 412-416. The horizontal axes 406-410 represent time while the vertical axes 412-416 represent the strength or magnitude of the signal. The cardiac signals 400-404 may be slightly offset above or below the horizontal axes 406-410. A timeline 420 that is common to the cardiac signals 400-404 is provided to enable comparison of the timing of events represented by the cardiac signals 400-404 and the impact of overdriving the heart 102 on the events.

With respect to the first cardiac signal 400, the first cardiac signal 300 may represent the signal sensed by the IMD 100 (shown in FIG. 1) when the IMD 100 does not overdrive the heart 102 (shown in FIG. 1) and fusion occurs between a paced ventricular contraction and an intrinsic ventricular event. The first cardiac signal 400 includes a P-wave 418 that is representative of an atrial event. For example, the P-wave 418 may represent contraction of an atrium caused by application of a stimulus pulse to the atrium. The P-wave 418 occurs at an initial time referred to as $t_0$ on the timeline 420. After delivery of the stimulus pulse to the atrium at $t_0$, the IMD 100 monitors the first cardiac signal 400 to determine if capture of the atrial stimulus pulse occurs in a ventricle. The IMD 100 examines the first cardiac signal 400 to identify whether capture occurs within a predetermined capture window 422. The capture window 422 expires at a time referred to as $t_{CW}$ on the timeline 320. The IMD 100 may examine the first cardiac signal 400 to determine if capture has occurred by determining whether any waveforms representative of ventricular contraction occur before expiration of the capture window 422. For example, the IMD 100 may monitor the first cardiac signal 400 to determine if one or more of a Q-wave, an R-wave or an S-wave of a QRS complex occurs before the capture window 422 lapses. In the illustrated example, none of a Q-wave, R-wave or S-wave occurs prior to expiration of the capture window 422.

In the absence of overdriving the heart 102 (shown in FIG. 1), the IMD 100 (shown in FIG. 1) delivers a back-up stimulus pulse to a ventricle if a ventricular event is not detected during the capture window 422. For example, the IMD 100 may supply a ventricular stimulus pulse to the ventricle if capture of the atrial stimulus pulse is not detected during the capture window 422 or before $t_{CW}$. The application of the back-up stimulus pulse to the ventricle is represented by a ventricular stimulus pulse spike 424 in the first cardiac signal 400. The delivery of the back-up stimulus pulse results in a paced ventricular contraction, represented by a paced R-wave 426 and a paced S-wave 428. As shown in the first cardiac signal 400, however, the atrial stimulus pulse may have resulted in an intrinsic ventricular event. For example, the atrial stimulus pulse may have resulted in capture in a ventricle and caused ventricular contraction in the absence of delivery of the back-up stimulus pulse. For example, an intrinsic Q-wave 430 occurring prior to the ventricular stimulus pulse spike 424 may indicate that the atrial stimulus pulse caused an intrinsic ventricular contraction. As shown in the first cardiac signal 400, the paced ventricular event (for example, application of the back-up stimulus pulse) and the intrinsic ventricular event (for example, capture of the atrial stimulus pulse in the ventricle) occur at approximately the same time or during the same time period. As a result, fusion between the intrinsic ventricular event and the back-up stimulus pulse occurred, resulting in mixture of the intrinsic ventricular contraction and the paced ventricular contraction.

In order to reduce the occurrence of fusion between the paced and intrinsic ventricular events, the AV conduction time 302 (shown in FIG. 3) is increased by overdriving the heart 102 (shown in FIG. 1). For example, returning to the discussion of the method 200 in FIG. 2 with continued reference to the second and third cardiac signals 402, 404 shown in FIG. 4, at 214, the heart 102 is paced at the overdrive rate. For example, an atrium of the heart 102 may be paced at the overdrive rate.

With respect to the second cardiac signal 402, the atrial stimulus pulse applied at 214 is delivered at a stimulus output that exceeds the stimulation threshold. For example, the atrial stimulus pulse is applied at a sufficiently large electrical potential to cause capture in a corresponding ventricle of the heart 102 (shown in FIG. 1). Additionally, the atrial stimulus pulse is delivered at the overdrive rate to increase the AV conduction time 302 (shown in FIG. 3) of the heart 102. As described above, as the AV conduction time 302 increases, an AV delay 436 also increases. The AV delay 436 begins at approximately the same time that the P-wave 432 of the second cardiac signal 402 begins and terminates at a time referred to as $t_{AVD}$ on the timeline 420.

At 216, the IMD 100 (shown in FIG. 1) monitors the second cardiac signal 402 for an evoked response of the heart 102 (shown in FIG. 1) during the AV delay 436 or until $t_{AVD}$ to determine if capture of the atrial stimulus pulse applied at 214 occurs. As shown in the second cardiac signal 402, the evoked response of the heart 102 may include all or part of a QRS complex 438 composed of a Q-wave 440, an R-wave 442 and an S-wave 444 that occurs before expiration of the AV delay 436 and before $t_{AVD}$. As the QRS complex 438 represents a ventricular event, the IMD 100 may determine that the QRS complex 438 (or one or more of the Q-wave 440, the R-wave 442 and the S-wave 444) indicates ventricular capture of the atrial stimulus pulse. If the IMD 100 determines that capture has occurred, then flow of the method 200 proceeds to 218. In the example represented by the second cardiac signal 402, capture has occurred and the method 200 proceeds to 218.

At 218, a determination is made as to whether a loss of capture previously has been detected during the threshold search. As described above, the threshold search may incrementally lower the stimulus output until loss of capture is detected in a predetermined number of consecutive cardiac cycles. If the threshold search is in the process of incrementally lowering the stimulus output and no loss of capture previously has been detected during the current threshold search, then the lack of a previously detected loss of capture during the threshold search may indicate that the threshold search is in the process of lowering the stimulus output until a loss of capture occurs in the predetermined number of consecutive cardiac cycles. If no loss of capture previously has been detected during the current threshold search, flow of the method 200 continues to 220. At 220, the stimulus output is lowered by a predetermined amount, as described above. The flow of the method 200 then returns to 214 where the heart 102 (shown in FIG. 1) continues to be paced at the overdrive rate during the threshold search. Alternatively, the flow of the method 200 may return to 216 to update or determine a new overdrive rate. The threshold search may then continue to pace the heart 102 at the overdrive rate while lowering the stimulus output until a loss of capture occurs, as described above.

On the other hand, if it is determined at 218 that a loss of capture previously has been detected during the threshold search, then the previous loss of capture may indicate that the threshold search is in the process of incrementally increasing the stimulus output until capture occurs in a predetermined number of consecutive cardiac cycles. For example, the threshold search may already have lowered the stimulus output until a loss of capture was detected in the predetermined number of consecutive cardiac cycles and the threshold search is now in the process of increasing the stimulus output until the stimulus output exceeds the stimulus threshold of the heart 102 (shown in FIG. 1). If a loss of capture previously was detected during the current threshold search, then flow of the method 200 continues to 222.

At 222, a determination is made as to whether capture has been detected during the current threshold search in a predetermined number of consecutive cardiac cycles. If capture has been found in the predetermined number of consecutive cardiac cycles, including the current cardiac cycle, then the detection of capture in the cardiac cycles may indicate that the current stimulus output exceeds the stimulation threshold of the heart 102 (shown in FIG. 1). As a result, at 224, the stimulation threshold is set to be at least as great as the stimulus output of the current or recently applied stimulus pulse. For example, if the most recently applied stimulus pulse at 214 was applied at approximately 0.7 Volts and capture has been detected in the predetermined number of consecutive cardiac cycles using a stimulus output of approximately 0.7 Volts, then the threshold search may conclude by determining that the stimulation threshold of the heart 102 is approximately 0.7 Volts. Thus, the stimulation threshold is set to be at least as great as approximately 0.7 Volts. Alternatively, the stimulation threshold may be set to be a predetermined amount greater than the current or recently applied stimulus pulse.

On the other hand, if, at 222, it is determined that capture has not been detected in at least the predetermined number of consecutive cardiac cycles, then flow of the method 200 returns to 214, where the heart 102 (shown in FIG. 1) continues to be paced at the overdrive rate. Alternatively, flow of the method 200 may return to 212 where the overdrive rate is updated or a new overdrive rate is determined.

Returning to the analysis performed at 216, if the stimulus output of the stimulus pulses applied to the heart 102 (shown in FIG. 1) does not exceed the stimulation threshold of the heart 102, then the stimulus pulses applied at 214 may not result in ventricular capture. The third cardiac signal 404 shown in FIG. 4 represents application of an atrial stimulus pulse at 214 that does not result in ventricular capture. With respect to the third cardiac signal 404, at 216, the IMD 100 (shown in FIG. 1) monitors the third cardiac signal 404 over the AV delay 436, or until $t_{AVD}$, to determine whether capture of the stimulus pulse applied at 214 occurs. As shown in FIG. 4, no intrinsic ventricular event occurs prior to expiration of the AV delay 436 or prior to $t_{AVD}$. As a result, at 216, the IMD 100 determines that a loss of capture has occurred and flow of the method 200 continues to 226.

At 226, a back-up stimulus pulse is applied to the heart 102 (shown in FIG. 1). For example, a back-up stimulus pulse may be supplied to a ventricle to ensure ventricular contraction. The delivery of the back-up stimulus pulse is represented by a ventricular stimulus pulse spike 446 in the third cardiac signal 404. The back-up stimulus pulse causes a ventricular event represented by an evoked response waveform 448 of the third cardiac signal 404. The evoked response waveform 448 may include a paced Q-wave 450 and/or a paced R-wave 452. The paced Q-wave 450 and the paced R-wave 452 may indicate contraction of the ventricle caused by the back-up stimulus pulse.

After applying the back-up stimulus pulse, at 228, a determination is made as to whether a loss of capture has occurred during the current threshold search for a predetermined number of consecutive cardiac cycles. For example, the loss of capture in the third cardiac signal 404 that was detected at 216 may be one of a series of losses of capture in consecutive cardiac cycles. If the number of consecutive cardiac cycles, including the current cardiac cycle, meets or exceeds the predetermined number of consecutive cardiac cycles, then the current loss of capture may indicate that the threshold search has sufficiently lowered the stimulus output of the stimulus pulses below the stimulation threshold of the heart 102 (shown in FIG. 1). As a result, at 230, the stimulus output of subsequent stimulus pulses is increased at 230. For example, the electrical potential of subsequent stimulus pulses applied to the heart 102 at 216 may be increased by at least a predetermined amount.

On the other hand, if, at 228, the IMD 100 (shown in FIG. 1) determines that a loss of capture has not occurred in at least the predetermined number of consecutive cardiac cycles, then the loss of capture detected in the most recent or current cardiac cycle may not indicate that the threshold search has sufficiently lowered the stimulus output of the stimulus pulses below the stimulation threshold. For example, the threshold search may continue to apply the stimulus pulses at 214 at the current stimulus output to determine whether one or more subsequent cardiac cycles also exhibit a loss of capture at the current stimulus output. If a loss of capture has not occurred in at least the predetermined number of consecutive cardiac cycles, or if the stimulus output of the stimulus pulses has been increased at 230, flow of the method 200 returns to 214, where the heart 102 (shown in FIG. 1) continues to be paced at the overdrive rate. For example, the method 200 may return to 214 to continue the threshold search while overdriving the heart 102. Alternatively, flow of the method 200 may return to 212 where the overdrive rate at which the heart 102 is paced is updated or a new overdrive rate is determined.

Figure 5:
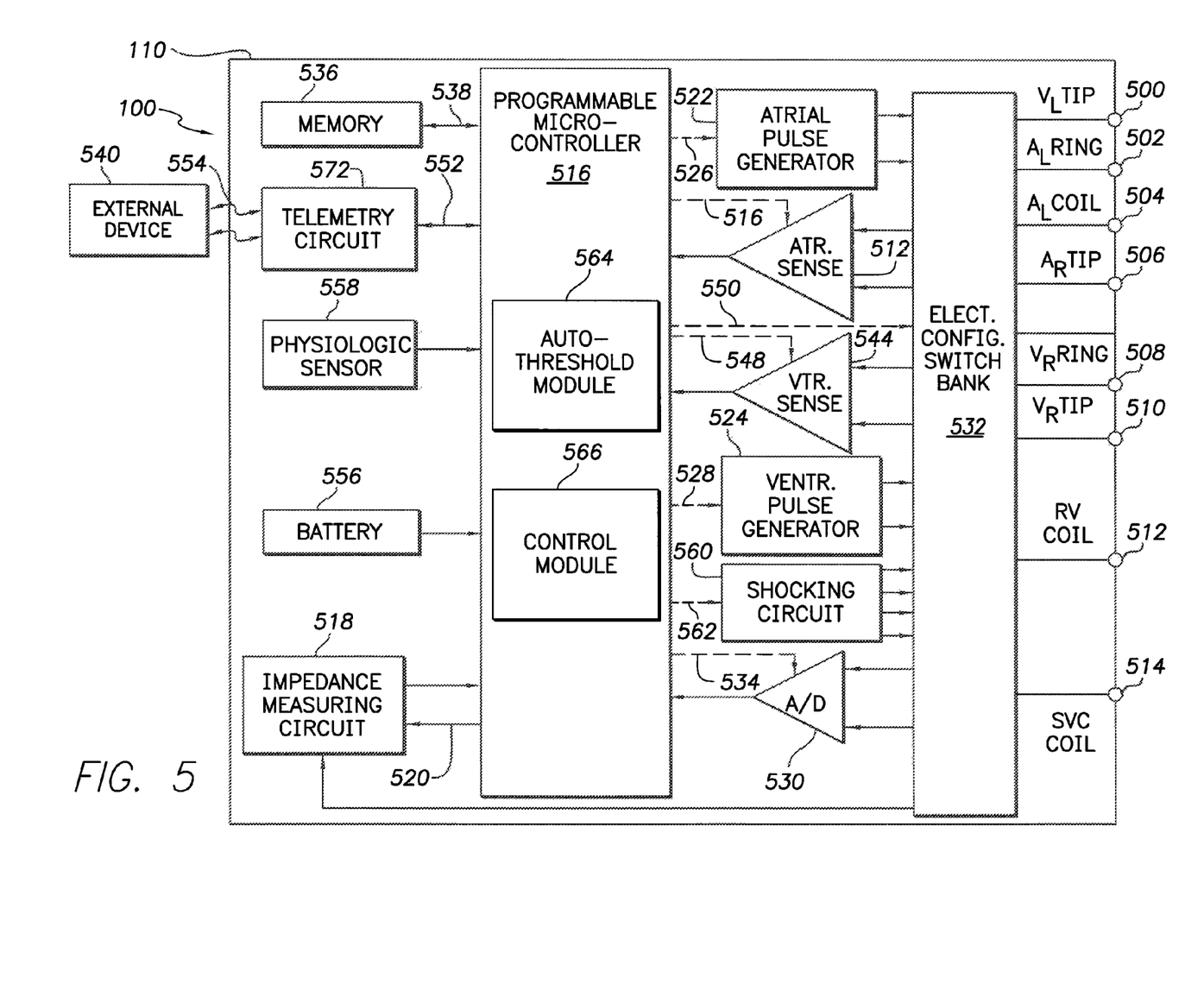
FIG. 5 illustrates a block diagram of exemplary internal components of the IMD shown in FIG. 1.

FIG. 5 illustrates a block diagram of exemplary internal components of the IMD 100. The housing 110 of the IMD 100 includes several inputs to receive signals measured or sensed by the electrodes 112-128 (shown in FIG. 1). The inputs may include one or more of an LV tip input ($V_L$ TIP) 500, an LA ring input ($A_L$ RING) 502, an LA coil input ($A_L$ COIL) 504, an RA tip input ($A_R$ TIP) 506, an RV ring input ($V_R$ RING) 508, an RV tip input ($V_R$ TIP) 510, an RV coil input 512 and an SVC coil input 514. As the names of the inputs 500-514 imply, the inputs 500-514 are electrically coupled with the corresponding electrodes 112-128 (shown in FIG. 1). For example, the LV tip input 500 may be connected with the LV tip electrode 116 (shown in FIG. 1); the LA ring input 502 may connected with the LA ring electrode 118 (shown in FIG. 1); the LA coil input 504 may be connected with the LA coil electrode 120 (shown in FIG. 1); the RA tip input 506 may be connected with the RA tip electrode 112 (shown in FIG. 1); the RV ring input 508 may be connected with the RV ring electrode 124 (shown in FIG. 1); the RV tip input 510 may be connected with the RV tip electrode 122 (shown in FIG. 1); the RV coil input 512 may be connected with the RV coil electrode 126 (shown in FIG. 1); and the SVC coil input 514 may be connected with the SVC coil electrode 128 (shown in FIG. 1).

The IMD 100 includes a programmable microcontroller 516, which controls the operation of the IMD 100 based on sensed cardiac signals. The microcontroller 516 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. The microcontroller 516 receives, processes, and manages storage of digitized data from the various electrodes 112-128 (shown in FIG. 1). The microcontroller 516 operates to perform threshold searching to adjust the stimulus output of the stimulus pulses. The microcontroller 516 may overdrive an atrium of the heart 102 (shown in FIG. 1) during a threshold search in accordance with one or more embodiments of the method 200 (shown in FIG. 2) described above.

The cardiac signals sensed by the electrodes 112-128 (shown in FIG. 1) are communicated through the inputs 500-514 to an electronically configured switch bank, or switch, 532. The switch 532 includes a plurality of switches for connecting the desired electrodes 112-128 and inputs 500-514 to the appropriate I/O circuits. The switch 532 closes and opens switches to provide electrically conductive paths between the circuitry of the IMD 100 (shown in FIG. 1) and the inputs 500-514 in response to a control signal 550. The cardiac signals are then communicated to an analog-to-digital (A/D) data acquisition system 530. The microcontroller 516 determines which of the cardiac signals are communicated to the data acquisition system 530. The data acquisition system 530 converts the raw analog data of the sensed cardiac signals into digital signals and communicates the digital signals as cardiac signal waveforms to the microcontroller 516. A control signal 534 from the microcontroller 516 determines when the data acquisition system 530 acquires signals, stores the signals in a memory 536 via a data/address bus 538, or transmits data to an external device 540 via a telemetry circuit 572.

An impedance measuring circuit 518 may be electrically coupled to the switch 532 so that a potential difference between desired pairs of the housing 110 and the electrodes 112-128 (shown in FIG. 1) may be obtained. The impedance measuring circuit 518 is enabled by the microcontroller 516 via a control signal 520. An atrial sensing circuit 542 and a ventricular sensing circuit 544 are selectively coupled to the leads 104-108 (shown in FIG. 1) and the electrodes 112-128 through the switch 532 for sensing cardiac activity in the chambers of the heart 102 (shown in FIG. 1). Control signals 546, 548 from the microcontroller 516 direct output of the atrial and ventricular sensing circuits 542, 544.

An atrial pulse generator 522 and a ventricular pulse generator 524 each are configured to generate the stimulation pulses to the atrial and ventricular chambers of the heart 102 (shown in FIG. 1), respectively. For example, the atrial pulse generator 522 supplies the atrial stimulus pulses used to overdrive an atrium during a threshold search and the ventricular pulse generator 524 delivers the ventricular stimulus pulses to the corresponding ventricle if the atrial stimulus pulses are not captured in the ventricle. The pulse generators 522, 524 are controlled via corresponding control signals 526, 528 from the microcontroller 516 to trigger the stimulation pulses.

The microcontroller 516 includes modules that perform the threshold searches and the overdriving of an atrium during threshold searches, as described above. The modules carry out the operations described in connection with one or more embodiments of the method 200 (shown in FIG. 2). An autothreshold module 564 directs the threshold searches when the IMD 100 is operating in an autothreshold mode. The autothreshold module 564 enters into the autothreshold mode when a threshold search is to be conducted. For example, the autothreshold module 564 may enter the autothreshold mode when two consecutive cardiac cycles exhibit a loss of capture in a ventricle. During the threshold search, the autothreshold module 564 directs the atrial pulse generator 522 to apply atrial stimulus pulses to an atrium of the heart 102 (shown in FIG. 1) at the overdrive rate, as described above. The autothreshold module 564 directs the atrial pulse generator 522 to adjust the stimulus output of stimulus pulses applied during the threshold searches in order to identify the stimulation threshold. The autothreshold module 564 also directs the ventricular pulse generator 524 to deliver ventricular stimulus pulses as back-up stimulus pulses. For example, the autothreshold module 564 may cause the ventricular pulse generator 524 to supply a ventricular stimulus pulse when the AV delay 322 (shown in FIG. 3) expires after the atrial stimulus pulse with no detection of capture in the ventricle.

A control module 566 obtains, measures and calculates various parameters used during the threshold searches and the overdriving of an atrium. For example, the control module 566 determines the AV conduction time 302 (shown in FIG. 3) based on cardiac signals sensed by the electrodes 112-128 (shown in FIG. 1). The control module 566 obtains and applies the overdrive AV adjustment 318 (shown in FIG. 3) to the AV conduction time 302 in order to generate the AV delay 322 (shown in FIG. 3).

The memory 536 may be embodied in a computer-readable storage medium such as a ROM, RAM, flash memory, or other type of memory. The microcontroller 516 is coupled to the memory 536 by the data/address bus 538. The memory 536 may store programmable operating parameters and thresholds used by the microcontroller 516, as required, in order to customize operation of IMD 100 to suit the needs of a particular patient. The memory 536 may store data indicative of cardiac signals sensed by the electrodes 112-128 (shown in FIG. 1). The operating parameters of the IMD 100 may be non-invasively programmed into the memory 536 through the telemetry circuit 572 in communication with the external device 540, such as a trans-telephonic transceiver or a diagnostic system analyzer. The telemetry circuit 572 is activated by the microcontroller 516 by a control signal 552. The telemetry circuit 572 allows cardiac signals, intra-cardiac electrograms, impedance measurements, status information, and other data relating to the operation of IMD 100 to be sent to the external device 540 through an established communication link 554.

In the case where IMD 100 is intended to operate as an ICD device, the IMD 100 detects the occurrence of a shift in one or more waveforms in sensed cardiac signals that indicates an arrhythmia, and automatically applies an appropriate electrical shock therapy to the heart 102 (shown in FIG. 1) aimed at terminating the detected arrhythmia. To this end, the microcontroller 516 further controls a shocking circuit 560 by way of a control signal 562. The shocking circuit 560 generates shocking pulses of low (up to 0.5 joules), moderate (0.5-10 joules) or high energy (11 to 40 joules). Such shocking pulses are applied to the heart 102 of the patient through at least two shocking electrodes, and as shown in this embodiment, selected from the LA coil electrode 120 (shown in FIG. 1), the RV coil electrode 126 (shown in FIG. 1), and/or the SVC coil electrode 128 (shown in FIG. 1).

A battery 556 provides operating power to the circuits of the IMD 100, including the microcontroller 516. The IMD 100 also includes a physiologic sensor 558 that may be used to adjust pacing stimulation rate according to the exercise state of the patient.

Figure 6:
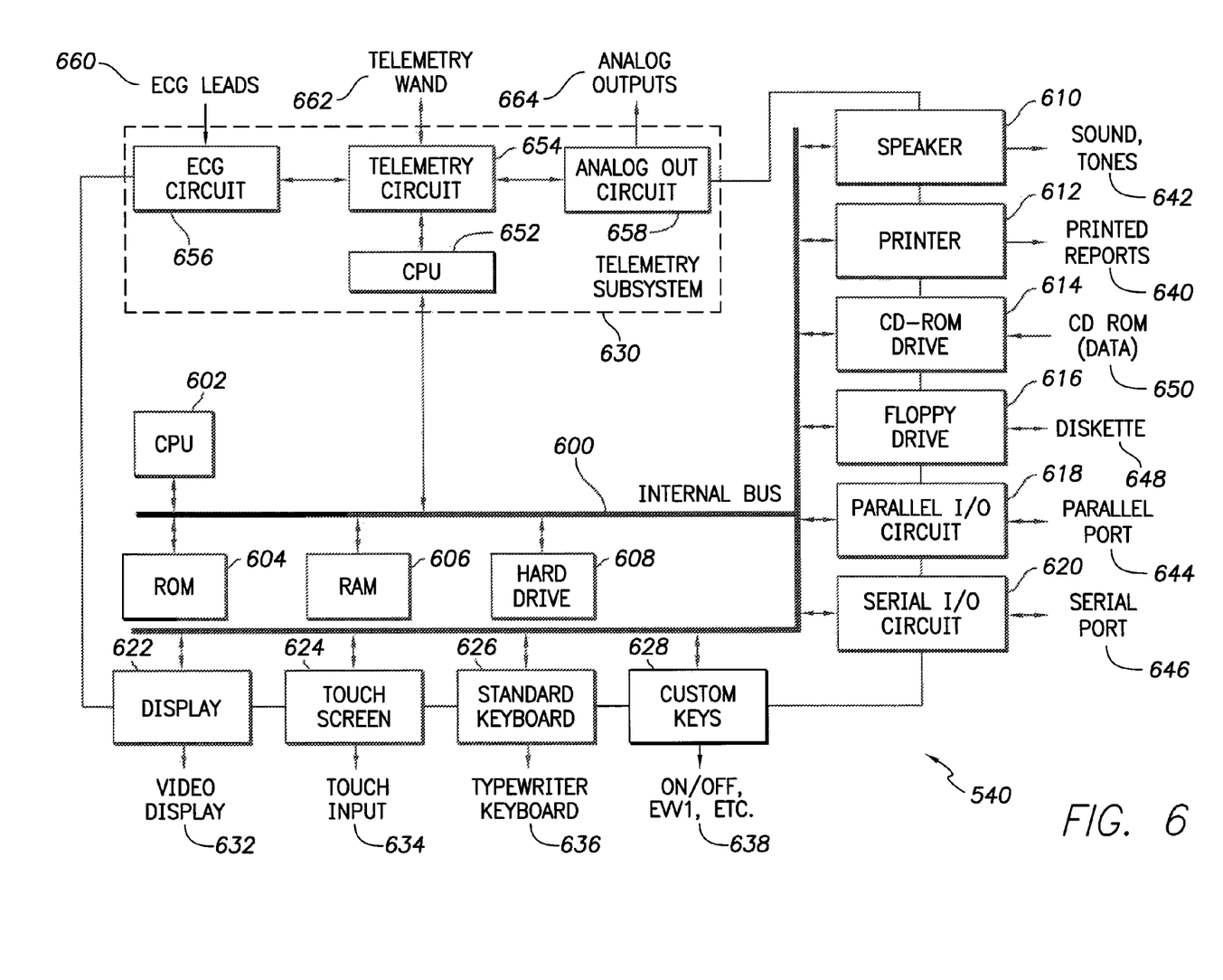
FIG. 6 illustrates a functional block diagram of an external device shown in FIG. 5 according to one embodiment.

FIG. 6 illustrates a functional block diagram of the external device 540 according to one embodiment. The external device 540 may be used by a physician or operator of the IMD 100 (shown in FIG. 1) to interface with the IMD 100. The external device 540 may be used to upload and/or download data relevant to threshold searches. For example, the external device 540 may download stimulation thresholds derived by the threshold searches performed by the IMD 100 and upload predetermined values for the overdrive AV adjustment 318 (shown in FIG. 3) or the AV delay 322 (shown in FIG. 3).

The external device 540 includes an internal bus 600 that connects/interfaces with a Central Processing Unit (CPU) 602, ROM 604, RAM 606, a hard drive 608, the speaker 610, a printer 612, a CD-ROM drive 614, a floppy drive 616, a parallel I/O circuit 618, a serial I/O circuit 620, the display 622, a touch screen 624, a standard keyboard connection 626, custom keys 628, and a telemetry subsystem 630. The internal bus 600 is an address/data bus that transfers information between the various components described herein. The hard drive 608 may store operational programs as well as data, such as AV conduction times 302 (shown in FIG. 3), overdrive AV adjustments 320 (shown in FIG. 3), AV delays 322 (shown in FIG. 3), and the like.

The CPU 602 typically includes a microprocessor, a microcontroller, or equivalent control circuitry, to control interfacing with the external device 540 and the IMD 100 (shown in FIG. 1). The CPU 602 may include memory, logic and timing circuitry, state machine circuitry, and I/O circuitry to interface with the IMD 100. The display 622 (e.g., may be connected to the video display 632) and the touch screen 624 display information relating to the IMD 100. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 (e.g., EWI) the external device 540. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 includes a central processing unit (CPU) 652 in electrical communication with a telemetry circuit 654, which communicates with both an ECG circuit 656 and an analog out circuit 658. The ECG circuit 656 is connected to ECG leads 660. The telemetry circuit 654 is connected to a telemetry wand 662. The analog out circuit 658 includes communication circuits to communicate with analog outputs 664. The external device 540 may communicate with the IMD 100 (shown in FIG. 1) via a hard-wired connection or via a wireless connection.

Figure 7:
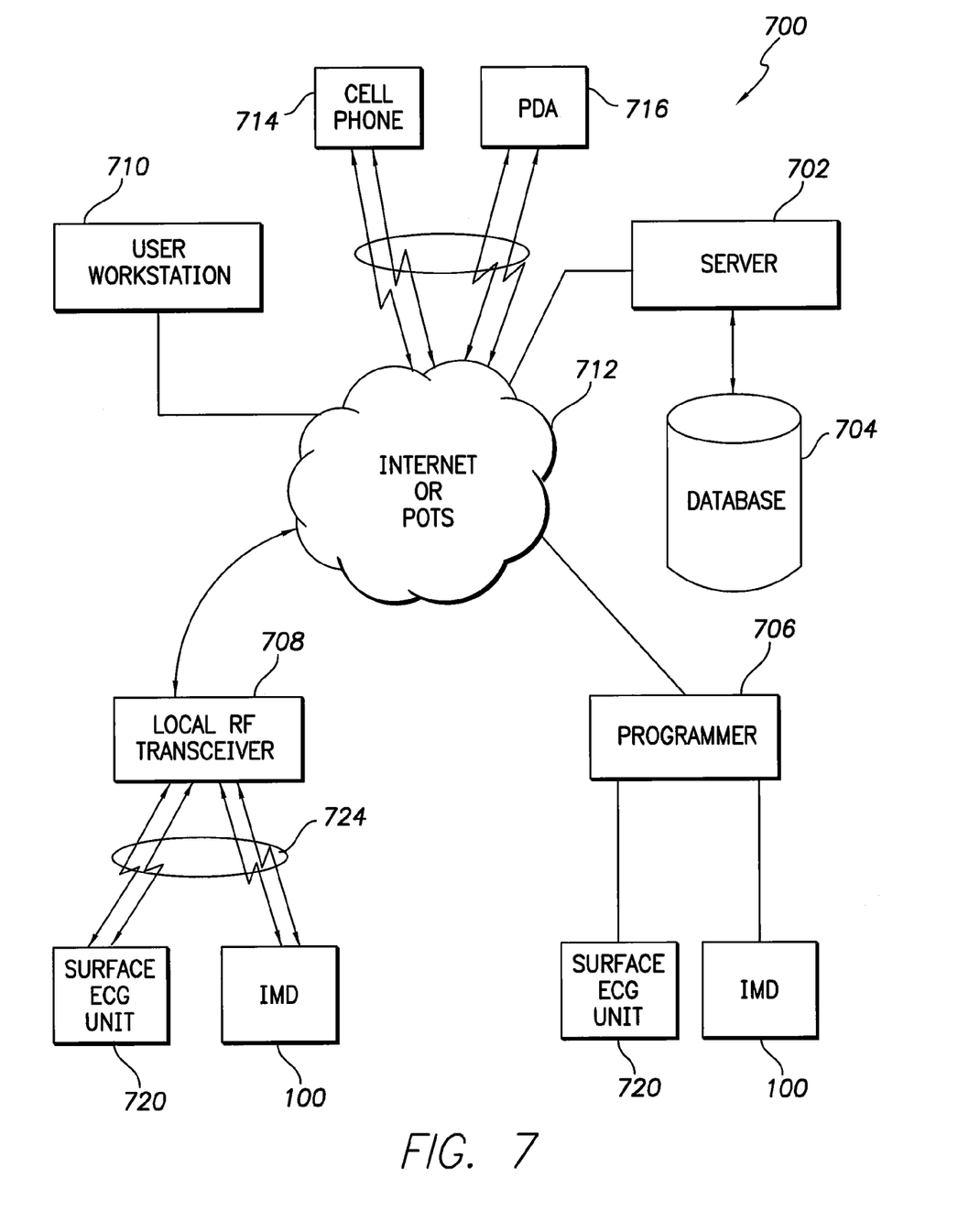
FIG. 7 illustrates a distributed processing system that may be used to communicate data obtained and used in connection with the process shown in FIG. 2 in accordance with one embodiment.

FIG. 7 illustrates a distributed processing system 700 that may be used to communicate data obtained and used in connection with the method 200 shown in FIG. 2 and described above in accordance with one embodiment. For example, the system 700 may be used to communicate data relevant to threshold searches, such as stimulation thresholds derived by the threshold searches, the overdrive AV adjustment 318 (shown in FIG. 3) and the AV delay 322 (shown in FIG. 3). The distributed processing system 700 includes a server 702 connected to a database 704, a programmer 706 (e.g., similar to external device 540 shown in FIG. 5), a local RF transceiver 708 and a user workstation 710 electrically connected to a communication system 712. The communication system 712 may be a network such as a LAN, a campus area network (CAN), a metropolitan area network (MAN), a wide area network (WAM), the Internet, a voice over IP (VoIP) gateway, a local plain old telephone service (POTS), a cellular phone based network, and the like. The communication system 712 facilitates the transfer/receipt of information such as stimulation thresholds, AV conduction times 302 (shown in FIG. 3), overdrive AV adjustments 320 (shown in FIG. 3), AV delays 322 (shown in FIG. 3), and the like. The server 702 is a computer system that controls communication of information such as stimulation thresholds, AV conduction times 302, overdrive AV adjustments 320, AV delays 322, and the like. The server 702 interfaces with the communication system 712 to transfer information between the programmer 706, the local RF transceiver 708, the user workstation 710 as well as a cell phone 714, and a personal data assistant (PDA) 716 to the database 704 for storage/retrieval of records of information. On the other hand, the server 702 may upload raw cardiac signals from a surface ECG unit 720 or the IMD 100 via the local RF transceiver 708 or the programmer 706.

The database 704 stores information such as cardiac signals, stimulation thresholds, AV conduction times 302 (shown in FIG. 3), overdrive AV adjustments 320 (shown in FIG. 3), AV delays 322 (shown in FIG. 3), and the like for a single or multiple patients. The information is downloaded into the database 704 via the server 702 or, alternatively, the information is uploaded to the server from the database 704. The programmer 706 is similar to the external device 540 (shown in FIG. 5) and may reside in a patient's home, a hospital, or a physician's office. Programmer 706 interfaces with the surface ECG unit 720 and the IMD 100. The programmer 706 may wirelessly communicate with the IMD 100 or communicate via a hard-wired connection. The programmer 706 is able to acquire cardiac signals from the surface of a person (e.g., ECGs), intra-cardiac electrogram (e.g., IEGM) signals from the IMD 100. The programmer 706 interfaces with the communication system 712, either via the internet or via POTS, to upload the information acquired from the surface ECG unit 720 or the IMD 100 to the server 702.

The local RF transceiver 708 interfaces with the communication system 712, via a communication link 724, to upload cardiac signals acquired from the surface ECG unit 720 and/or other data acquired from the IMD 100 to the server 702. In one embodiment, the surface ECG unit 720 and the IMD 100 have a bidirectional connection with the local RF transceiver 708 via a wireless connection. On the other hand, the local RF transceiver 708 may download stored data, and the like, from the database 704 to the surface ECG unit 720 or the IMD 100. The user workstation 710 may interface with the communication system 712 to download information via the server 702 from the database 704. Alternatively, the user workstation 710 may download raw data from the surface ECG unit 720 or IMD 100 via either the programmer 706 or the local RF transceiver 708. The user workstation 710 may download the information and notifications to the cell phone 714, the PDA 716, the local RF transceiver 708, the programmer 706, or to the server 702 to be stored on the database 704.

Figure 8:
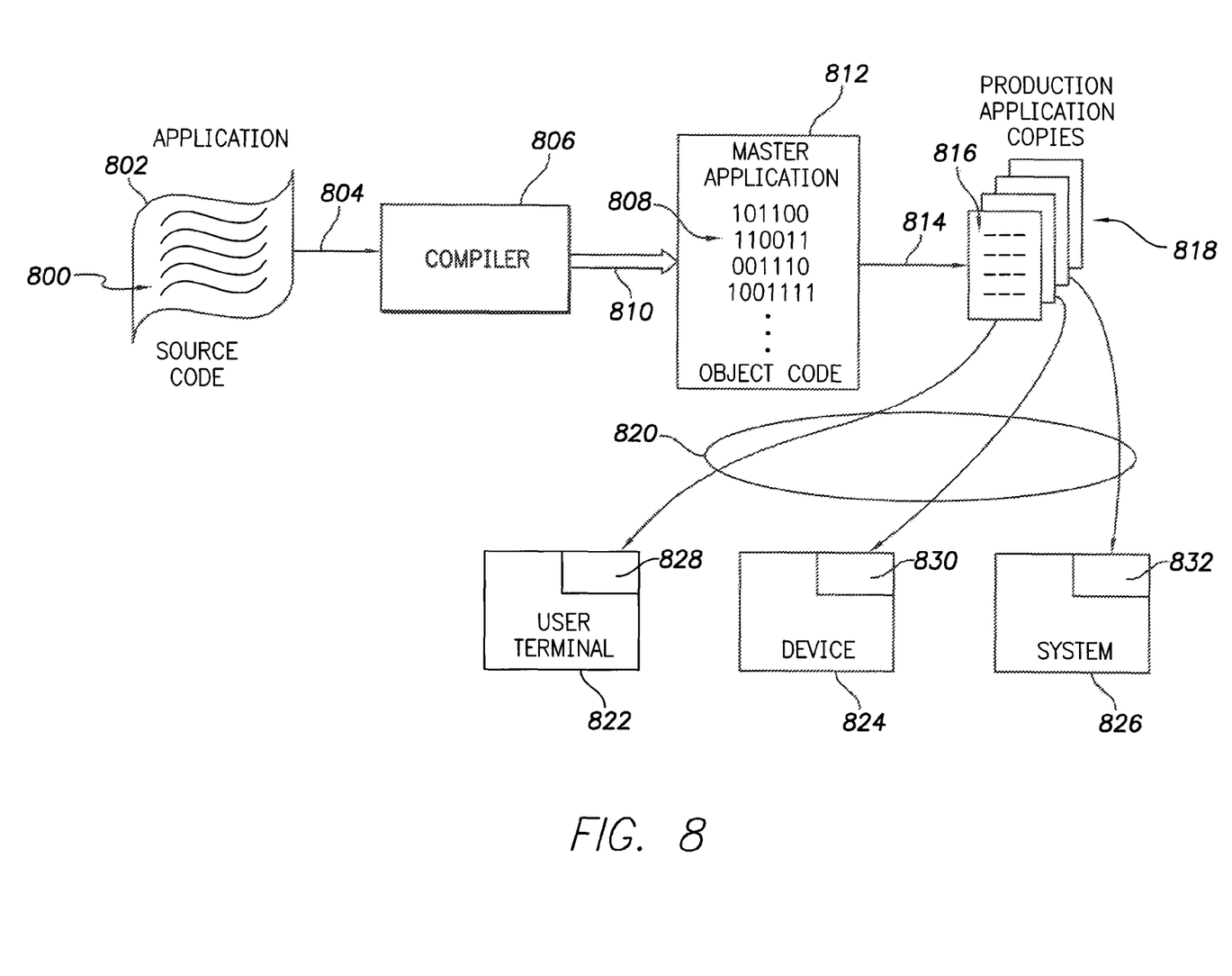
FIG. 8 illustrates a block diagram of exemplary manners in which embodiments of the present invention may be stored, distributed, and installed on a computer-readable medium.

FIG. 8 illustrates a block diagram of exemplary manners in which embodiments of the present invention may be stored, distributed, and installed on a computer-readable medium. In FIG. 8, the "application" represents one or more of the methods and process operations discussed above. The application is initially generated and stored as source code 800 on a source computer-readable medium 802. The source code 800 is then conveyed over path 804 and processed by a compiler 806 to produce object code 808. The object code 808 is conveyed over path 810 and saved as one or more application masters on a master computer-readable medium 812. The object code 808 is then copied numerous times, as denoted by path 814, to produce production application copies 816 that are saved on separate production computer-readable medium 818. The production computer-readable medium 818 is then conveyed, as denoted by path 820, to various systems, devices, terminals and the like. A user terminal 822, a device 824 and a system 826 are shown as examples of hardware components, on which the production computer-readable medium 818 are installed as applications (as denoted by 828 through 832). For example, the production computer-readable medium 818 may be installed on the IMD 100 (shown in FIG. 1) and/or the microcontroller 516 (shown in FIG. 5). Examples of the source, master, and production computer-readable medium 802, 812, and 818 include, but are not limited to, CDROM, RAM, ROM, Flash memory, RAID drives, memory on a computer system, and the like. Examples of the paths 804, 810, 814, and 820 include, but are not limited to, network paths, the internet, Bluetooth, GSM, infrared wireless LANs, HIPERLAN, 3G, satellite, and the like. The paths 804, 810, 814, and 820 may also represent public or private carrier services that transport one or more physical copies of the source, master, or production computer-readable medium 802, 812 or 818 between two geographic locations. The paths 804, 810, 814 and 820 may represent threads carried out by one or more processors in parallel. For example, one computer may hold the source code 800, compiler 806 and object code 808. Multiple computers may operate in parallel to produce the production application copies 816. The paths 804, 810, 814, and 820 may be intra-state, inter-state, intra-country, inter-country, intra-continental, inter-continental, and the like.

The operations noted in FIG. 8 may be performed in a widely distributed manner world-wide with only a portion thereof being performed in the United States. For example, the application source code 800 may be written in the United States and saved on a source computer-readable medium 802 in the United States, but transported to another country (corresponding to path 804) before compiling, copying and installation. Alternatively, the application source code 800 may be written in or outside of the United States, compiled at a compiler 806 located in the United States and saved on a master computer-readable medium 812 in the United States, but the object code 808 transported to another country (corresponding to path 814) before copying and installation. Alternatively, the application source code 800 and object code 808 may be produced in or outside of the United States, but production application copies 816 produced in or conveyed to the United States (for example, as part of a staging operation) before the production application copies 816 are installed on user terminals 822, devices 824, and/or systems 826 located in or outside the United States as applications 828 through 832. As used throughout the specification and claims, the phrases "computer-readable medium" and "instructions configured to" shall refer to any one or all of (i) the source computer-readable medium 802 and source code 800, (ii) the master computer-readable medium and object code 808, (iii) the production computer-readable medium 818 and production application copies 816 and/or (iv) the applications 828 through 832 saved in memory in the terminal 822, device 824, and system 826.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable medical device comprising:
    a lead including electrodes configured to be positioned within a heart, at least one of the electrodes being capable of sensing cardiac signals;
    a pulse generator to deliver a stimulus pulse through at least one of the electrodes;
    an autothreshold module to perform a threshold search when operating in an autothreshold mode, the autothreshold module to cause atrial stimulus pulses to be delivered in an atrium of the heart at an overdrive rate during the threshold search; and
    a control module to determine an AV conduction time and to apply an overdrive AV adjustment to the AV conduction time to generate an AV delay, the autothreshold module to utilize the AV delay in connection with delivering ventricular stimulus pulses to a ventricle of the heart, wherein the control module measures the AV conduction time between atrial stimulus pulses while the autothreshold module is in the autothreshold mode.

2. The implantable medical device of claim 1, wherein the overdrive AV adjustment is predetermined and the control module shortens or lengthens the AV conduction time by the overdrive AV adjustment to generate the AV delay.

3. The implantable medical device of claim 1, wherein the control module measures the AV conduction time while the autothreshold module causes the atrial stimulus pulses to be delivered, and the control module calculates the overdrive AV adjustment based on the AV conduction time.

4. The implantable medical device of claim 1, wherein the control module measures cardiac signals over multiple cardiac cycles and calculates a cardiac rate based thereon, the control module determining the overdrive rate as a function of the cardiac rate.

5. The implantable medical device of claim 1, wherein the autothreshold module enters the autothreshold mode when a loss of capture is detected in at least two consecutive cardiac cycles.

6. The implantable medical device of claim 1, wherein the autothreshold module applies the atrial stimulation pulses and the ventricular stimulation pulses separated from one another by the AV delay.

7. The implantable medical device of claim 1, wherein the AV conduction time represents an elapsed time between applying the stimulus pulse to the atrium and a contraction in the ventricle.

8. The implantable medical device of claim 1, wherein the autothreshold module adjusts the atrial stimulus pulses during the threshold search.

9. A method for overdriving a heart chamber during a threshold search, the method comprising:
    delivering stimulus pulses to an atrium of the heart at an overdrive rate during the threshold search;
    determining an AV conduction time based on the stimulation pulses;
    applying an overdrive AV adjustment to the AV conduction time to generate an AV delay; and
    utilizing the AV delay in connection with delivering a stimulus pulse to a ventricle of the heart, wherein the determining operation comprises measuring the AV conduction time between stimulation pulses.

10. The method of claim 9, wherein the overdrive AV adjustment is predetermined and the applying operation comprises shortening or lengthening the AV conduction time by the overdrive AV adjustment to generate the AV delay.

11. The method of claim 9, wherein determining operation comprises measuring the AV conduction time while the delivering operation delivers the stimulation pulse, further wherein the applying operation comprises calculating the overdrive AV adjustment based on the AV conduction time.

12. The method of claim 9, further comprising measuring cardiac signals over multiple cardiac cycles, calculating a cardiac rate based thereon, and determining the overdrive rate as a function of the cardiac rate.

13. The method of claim 9, wherein the autothreshold module enters the autothreshold mode when a loss of capture is detected in at least two consecutive cardiac cycles.

14. The method of claim 9, wherein the atrial stimulation pulses and the ventricular stimulation pulses are delivered such that each atrial stimulation pulse is separated from each subsequent ventricular stimulation pulse by the AV delay.

15. The method of claim 9, wherein the AV conduction time represents an elapsed time between applying the stimulus pulse to the atrium and a contraction in the ventricle.

16. A non-transitory computer readable storage medium for use with an implantable medical device having a lead including electrodes configured to be positioned within a heart, a pulse generator and a microcontroller, the computer readable storage medium comprising instructions to:
    direct the pulse generator to deliver atrial stimulus pulses in an atrium of the heart at an overdrive rate during a threshold search; and
    direct the microcontroller to:
        determine an AV conduction time; and
        apply an overdrive AV adjustment to the AV conduction time to generate an AV delay,
    wherein the instructions direct the pulse generator to utilize the AV delay in connection with delivering ventricular stimulus pulses to a ventricle of the heart, wherein the instructions direct the microcontroller to measure the AV conduction time between atrial stimulus pulses during the threshold search.

17. The computer readable storage medium of claim 16, wherein the overdrive AV adjustment is predetermined and the instructions direct the microcontroller to shorten or lengthen the AV conduction time by the overdrive AV adjustment to generate the AV delay.

18. The computer readable storage medium of claim 16, wherein the instructions direct the microcontroller to measure the AV conduction time while directing the pulse generator to deliver the atrial stimulus pulses, further wherein the instructions direct the microcontroller to calculate the overdrive AV adjustment based on the AV conduction time.

19. The computer readable storage medium of claim 16, wherein the instructions direct the microcontroller to measure cardiac signals over multiple cardiac cycles and calculate a cardiac rate based thereon to determine the overdrive rate as a function of the cardiac rate.

20. The computer readable storage medium of claim 16, wherein the instructions direct the microcontroller to initiate the threshold search when a loss of capture is detected in at least two consecutive cardiac cycles.

21. The computer readable storage medium of claim 16, wherein the instructions direct the pulse generator to apply the atrial stimulation pulses and the ventricular stimulation pulses separated from one another by the AV delay.

22. The computer readable storage medium of claim 16, wherein the AV conduction time represents an elapsed time between applying the stimulus pulse to the atrium and a contraction in the ventricle.

* * * * *